(12) United States Patent
Deka et al.

(10) Patent No.: US 6,232,125 B1
(45) Date of Patent: May 15, 2001

(54) METHOD AND APPARATUS FOR DIFFERENTIATING AND ENUMERATING LEUKOCYTES

(75) Inventors: Chiranjit Deka, Miami; Mark A. Wells, Davie; Carlos M. Rodriguez; Carlos Reyes, both of Miami, all of FL (US)

(73) Assignee: Coulter International Corp., Miami, FL (US)

( * ) Notice: Subject to any disclaimer, the term of this patent is extended or adjusted under 35 U.S.C. 154(b) by 0 days.

(21) Appl. No.: 09/370,814

(22) Filed: Aug. 9, 1999

(51) Int. Cl.[7] .................................................. G01N 33/48
(52) U.S. Cl. .................. 436/63; 436/8; 436/10; 436/150; 436/164; 435/2; 422/73; 356/39; 356/317; 356/318; 356/337; 356/340
(58) Field of Search .................. 436/8, 10, 63, 436/149, 150, 164; 435/2; 422/73; 356/39, 73, 317, 318, 337, 340

(56) References Cited

U.S. PATENT DOCUMENTS

| | | | |
|---|---|---|---|
| 2,656,508 | 10/1953 | Coulter | 324/71.1 |
| 5,017,497 | * 5/1991 | de Grooth et al. | 436/63 |
| 5,125,737 | 6/1992 | Rodriguez et al. | 356/39 |
| 5,510,267 | 4/1996 | Marshall | 436/63 |
| 5,518,928 | * 5/1996 | Cremins et al. | 436/40 |
| 5,874,310 | * 2/1999 | Li et al. | 436/10 |
| 5,874,311 | * 2/1999 | Li et al. | 436/10 |
| 6,004,816 | * 12/1999 | Mizukami et al. | 436/10 |
| 6,067,157 | * 5/2000 | Altendorf | 356/337 |

OTHER PUBLICATIONS

Gilbert, et al., "Basophil Counting with a New Staining Method Using Alcian Blue", *Blood,* vol. 46, No. 2, pp. 279–286 (Aug.) 1975.
Hubl, et al., "Evaluation of Automated Basophil Counting by Using Fluorescence–Labelled Monoclonal Antibodies", *J. Clin. Lab. Anal.,* 10:177–183 (1996).
Terstappen, et al., "Four Parameter White Blood Cell Differential Counting Based on Light Scattering Measurements", *Cytometry,* 9:39–43 (1988).

* cited by examiner

*Primary Examiner*—Maureen M. Wallenhorst
(74) *Attorney, Agent, or Firm*—Warren W. Kurz; Mitchell E. Alter

(57) ABSTRACT

A method and apparatus for differentiating and enumerating the five major sub-populations of leukocytes in a blood sample (i.e., lymphocytes, monocytes, eosinophils, neutrophils and basophils) uses multiangle light scatter and DC (Coulter) volume measurements. Light scattering characteristics of the leukocytes are determined within five different angular ranges, all being lower than 40 degrees. The invention is particularly useful in differentiating and enumerating the basophil sub-population which has heretofore required more complex apparatus and/or chemical processing.

10 Claims, 6 Drawing Sheets

METHOD AND APPARATUS FOR DIFFERENTIATING AND ENUMERATING LEUKOCYTES

BACKGROUND OF THE INVENTION

1. Field of Invention

The present invention relates to improvements in methods and apparatus for differentiating and enumerating the five major sub-populations of leukocytes (white blood cells) in a human blood sample. The invention is particularly useful for differentiating and enumerating the basophil sub-population of leukocytes in a blood sample.

2. Discussion of the Prior Art

Conventional hematology instruments are capable of differentiating and enumerating the five major sub-populations of leukocytes (white cells) in a human blood sample, namely, the lymphocyte, monocyte, neutrophil, eosinophil and basophil sub-populations. Such instruments commonly operate by first lysing the erythrocytes (red cells) in a whole blood sample, and then causing the remaining leukocytes in the sample to flow, substantially one-at-a-time, through a narrow aperture or cell interrogation zone while subjecting each cell to a combination of electrical and light energy. While passing through the interrogation zone, a combination of measurements are made to determine each leukocyte's unique characteristics in terms of light scatter, Coulter DC volume, radio frequency (RF) electrical conductivity, polarization, and/or fluorescence. Of the five sub-populations of leukocytes, the basophils present a particularly difficult challenge to differentiate owing to (1) their relatively low number (compared to the number of other leukocytes in a normal human blood sample), and (2) their similarity to monocytes and lymphocytes in responding to electrical and light stimuli, whereby the basophils appear in a region of parameter space where monocytes and lymphocytes are also found. To further complicate matters, the basophils are often not readily distinguishable as a tight cluster in a scattergram in which two measured cell parameters are plotted against each other. This problem is discussed in the article by Terstappen et. al., Cytometry 9:39–43 (1988), where a scattergram obtained by comparing light scatter measurements at two different angular ranges, 1°–2.6° and 3°–11°, is used to resolve the three major populations of white blood cells, namely, the lymphocytes, monocytes and granulocytes which, in this case, include the eosinophil and neutrophil sub-populations). In this scattergram, the basophils were not resolvable as an independent cluster although a general region or "gated" area was tentatively given where the basophils tend to appear. However, it was the conclusion of the authors of that article that this gated area was not sufficient to obtain a reliable basophil count.

Other investigators have taken different approaches to solving the problem of differentiating and enumerating basophils. For example, in U.S. Pat. No. 5,125,737, Rodriguez et. al., the disclosure of which is incorporated herein by reference, the problem of overlapping lymphocyte and basophil sub-populations is addressed by using, in addition to DC volume measurements and light scatter measurements within certain relatively broad angular ranges between 10 degrees and 70 degrees, an additional measurement parameter termed "opacity" is used. Opacity is defined as the ratio of a cell's DC impedance (volume) to its RF conductivity. While useful in resolving the basophils from other leukocytes, this approach requires additional circuitry for producing the requisite RF electrical field in the cell-interrogation zone, as well as circuitry for detecting changes in the RF current, as occasioned by the passage of cells through the zone. Owing to signal-to-noise issues, this approach is not as simple as it may sound.

Another approach for differentiating basophils, used in the. H*1 Hematology Analyzer manufactured by Technicon, Inc., employs a two-step chemical process for differentially lysing the other leukocyte sub-populations. Obviously, the time needed for two sequential chemical processes and the cost of additional reagents are disadvantageous. Still another approach is disclosed by HubI et al. [J. Clin. Lab. Anal. 10:177–183 (1996)] where basophils are identified by using double staining with fluorescence-labeled monoclonal antibodies. Other special methods, such as staining of heparin within the basophils at low pH and in the presence of lanthanum ions, have also been used [Gilbert et. al., Blood, 46:279–286 (1975)] to resolve basophils. As suggested, all of these prior art approaches are relatively complex and, ideally, should be simplified.

In addition to the above-noted problem of resolving basophils in a whole blood sample, the eosinophil sub-population of leukocytes also requires special attention in providing a 5-part differential analysis. In some measurement schemes, eosinophils tend to "look like" neutrophils (i.e., in parameter space). The above-noted Terstappen et al. article also discloses the use of orthogonal depolarized light scatter and orthogonal total light scatter intensities to resolve eosinophils from the neutrophils. This method is based on an observation that the refractile granules in the eosinophils tend to induce a greater depolarization of the scattered light in the orthogonal direction. Since this depolarization effect is stronger for the eosinophils than the neutrophils, a scattergram obtained by comparing depolarized orthogonal light scatter with total orthogonal light scatter intensity resolves the eosinophils as a cluster separate from the neutrophils. The method of Terstappen et al. has been used subsequently by Marshal to resolve the eosinophil population in whole blood, as disclosed in U.S. Pat. No. 5,510,267. However, it is generally known that the polarization effect of light scatter is more subtle than angular dependence of total light scatter intensity. Therefore, in general, the detection system required to measure depolarization must be more sensitive than that required for discerning angular variation of total light scatter intensity.

SUMMARY OF THE INVENTION

In view of the foregoing discussion, an object of the present invention is to provide an improved method and apparatus for producing a five-part differential analysis of leukocytes in a whole blood sample, a method and apparatus that are improved from the standpoints that there is no requirement for RF (opacity) or depolarization measurements, or the use of monoclonal antibodies, fluorescent dyes, and/or multiple chemistry steps.

Another object of this invention is to provide a method for better differentiating the basophil and eosinophil sub-populations from other leukocyte sub-populations so that the basophils and eosinophils can be more accurately enumerated.

According to a preferred embodiment of the present invention, a five-part differential analysis of the leukocyte population in a whole blood sample is attained by a method comprising the steps of (a) producing first signals (DC) representative of the DC volume of individual leukocytes in the sample, and (b) producing a plurality of second signals (LS1–LS5) respectively representing the light-scattering properties of such leukocytes within five different angular ranges (AR1–AR5), each of such angular ranges being lower than 40 degrees measured with respect to the direction of propagation of an illuminating light beam. Preferably, four of the light-scattering ranges (AR1–AR4) are lower than 12 degrees, and the fifth angular range (AR5) is between about 20 and about 40 degrees. More preferably, the angular ranges lower than 12 degrees are: AR1=about 1 to about 3 degrees; AR2=about 4 to about 6 degrees; AR3= about 6 to about 8 degrees; and AR4=about 9 to about 12 degrees. Preferably, the DC volume and light scattering signals are processed according to an algorithm which first identifies and gates-out eosinophils based on signals derived from light-scattering measurements made in angular ranges AR1 and AR5; then identifies and gates-out monocytes, neutrophils, and the combination of lymphocytes and basophils based signals derived from DC volume and light-scattering measurements made in the angular range AR4; and finally differentiates basophils from lymphocytes based on signals derived from light scattering measurements made within the angular ranges AR2 and AR3. Preferably, the light-scattering signals derived from the measurements made in angular ranges AR1, AR2, AR3 and AR4 are processed in a pair of non-linear transformations which are then compared for the purpose forming a tighter, and hence, more readily distinguishable cluster of basophils in a scattergram.

Preferably, the method of the invention is carried out in an apparatus comprising an optical flow cell having a cell interrogation zone in which blood cells to be analyzed can be interrogated with optical and electrical energy. Such apparatus further includes (a) means for causing leukocytes in the sample to pass through the interrogation zone seriatim; (b) means for establishing a DC current flow through the interrogation zone while blood cells are passing therethrough, each of the blood cells being effective to modulate the DC current in the interrogation zone as a function of the cell's volume; (c) means for detecting the respective modulations in the DC current flow caused by the passage of individual cells passing through the interrogation zone to produce electrical signals proportional to each cell's volume; (d) means for illuminating individual blood cells passing through the interrogation zone with a beam of light propagating along an axis, each illuminated cell acting to scatter light incident thereon; (e) means for detecting the intensity of light scattered from an illuminated blood cell in the interrogation zone within the above-noted plurality of different angular ranges; and (f) means for differentiating the five major sub-populations of leukocytes in the sample, i.e., the lymphocyte, monocyte, neutrophil, eosinophil and basophil sub-populations, based on the respective amplitudes of the respective electrical signals produced by steps (c) and (e).

The invention will be better understood from the ensuing detailed description of preferred embodiments, reference being made to the accompanying drawings.

DETAILED DESCRIPTION OF PREFERRED EMBODIMENTS

Figure 1:
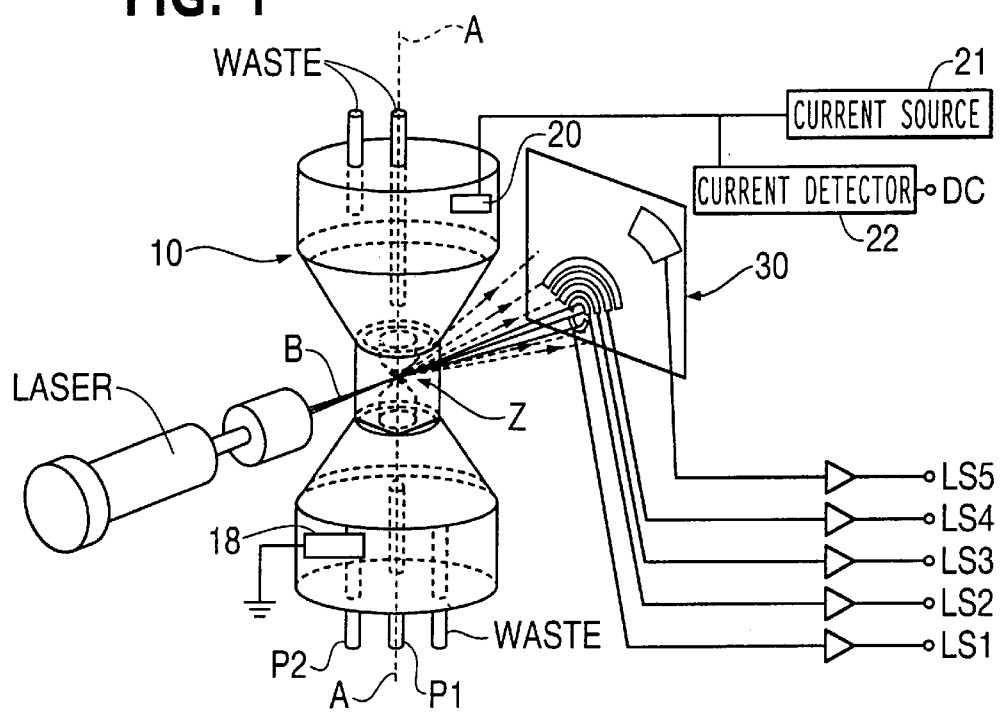
FIG. 1 is a schematic illustration of apparatus useful in implementing the method of the invention.

The most common parameter used for differentiating and counting the different types of blood cells in a whole blood sample is DC volume, often referred to as Coulter volume, after its discoverer, Wallace H. Coulter. As disclosed in Coulter's U.S. Pat. No. 2,656,508, the respective volumes of particles suspended in a dielectric liquid can be sensed by causing the particles to flow, one at a time (seriatim) through a small aperture while simultaneously sensing changes or modulations in a DC current flowing through the aperture. Whenever the conductivity of the particles differs from that of their suspending liquid, the electrical impedance of the aperture will vary as a function of the size (volume) of the particles within the aperture. Thus, by simply monitoring the amplitude of DC current passing through the aperture, the relative volume of each particle passing therethrough can be determined. For many years, DC volume alone was used to differentiate three sub-populations of blood cells, namely, monocytes, lymphocytes and granulocytes. As it became desirable to further differentiate the major sub-populations of granulocytes (i.e., the eosinophil, neutrophil and basophil sub-populations), additional parameters had to be found since all granulocytes tend to be similar in terms of DC volume. As indicated above, the light scatter parameter has also been used as a means for providing further information for differentiating cell types. The angular distribution of light scatter intensity from a microscopic particle or cell illuminated by a beam of incident light is a complex function of particle size and morphology. The scattered intensity varies as a complex oscillating function of the scattering angle. The number of peaks, the relative peak height and width, and the angular position at which they appear all depend on the physical characteristics of the measured particles and the measuring environment, such as the volume, internal structure, refractive index of the components of the particles, and the refractive index of the surrounding media.

According to a preferred embodiment of the present invention, a five-part differential analysis of the leukocyte population in a whole blood sample is attained by a method comprising the steps of (a) producing first signals representing the DC volume of individual leukocytes in the sample, (b) producing a plurality of second signals representing the respective light-scattering properties of each of such leukocytes within five different angular ranges (AR1–AR5), all being at an angle less than 40 degrees measured with respect to the direction of propagation of an illuminating light beam; and (c) differentiating and enumerating five different sub-populations of leukocytes based on such first and second signals. Preferably, four of the light-scattering ranges (AR1–AR4) are below 12 degrees, and the fifth angular range (AR5) is between about 20 and 40 degrees. More specifically, the angular ranges below 12 degrees are: AR1= about 1 to about 3 degrees; AR2=about 4 to about 6 degrees; AR3=about 6 to about 8 degrees; and AR4=about 9 to about 12 degrees.

According to a preferred embodiment of the invention, the DC volume and light scattering signals are processed according to an algorithm which (a) first identifies, enumerates and gates out eosinophils based on the light scattering measurements made in angular ranges AR1 and AR5; (b) then identifies, enumerates and gates out monocytes, neutrophils, and the combination of lymphocytes and basophils based on both the DC volume measurements and the light-scattering measurements made in angular range AR4; and (c) finally differentiates, enumerates and gates-out basophils from lymphocyte/basophil combination based on the light scattering measurements made in angular ranges AR2 and AR3. Preferably, the light-scattering signals, LS1, LS2, LS3 and LS4, derived from light-scattering measurements made within the angular ranges AR1, AR2, AR3 and AR4 are processed in a pair of non-linear transformations which, when plotted against each other, serve to enhance the clustering of the basophil population.

Figure 2:
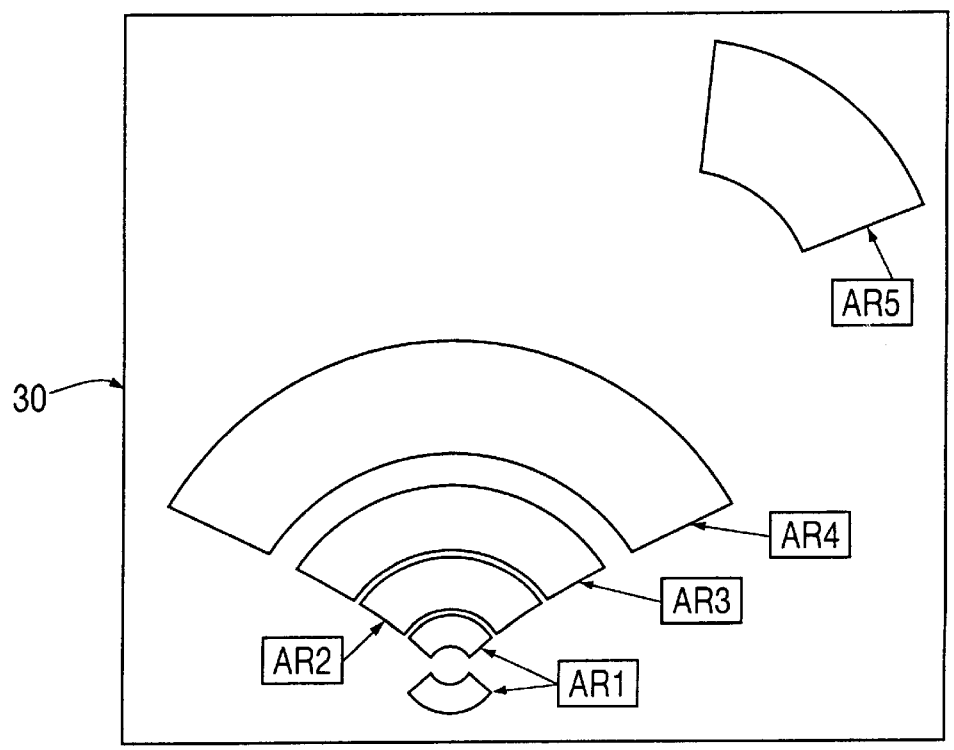
FIG. 2 is a plan view of a photo-detector useful in making the light-scattering measurements required by the method of the invention.

Apparatus for carrying out the method of the invention is illustrated schematically in FIG. 1. An optical flow cell 10 of the type disclosed, for example, in the aforementioned and commonly assigned U.S. Pat. No. 5,125,737, serves to direct a steady stream of leukocytes to be differentiated and enumerated through an interrogation zone Z located at the center of a Coulter aperture. A relatively pure sample of leukocytes is obtained, for example, by mixing a whole blood sample with a suitable lysing reagent (e.g. Erythrolyse™ lysing reagent, manufactured by Coulter Corporation, Miami, Fla.) to eliminate the erythrocytes (red cells) which typically outnumber the leukocytes (white cells) by about 800–1000:1. Alternatively, the red cells may be removed from the whole blood sample by a conventional Ficoll column, as explained below, through which the white and red cells settle out at different rates. The stream of leukocytes enter the flow cell through a port P1 and is hydrodynamically focused in a conventional manner along the central axis A of the cell interrogation zone via a sheath fluid introduced into the flow cell through a suitable port P2. A nominal current flow through the Coulter aperture is established by a pair of electrodes 18, 20, such electrodes being connected across a suitable DC current source 21 and DC current-sensing circuit 22. As noted above, the amplitude of the nominal current flow at any given time through the Coulter aperture depends on the volume of a cell passing therethrough, the larger the cell volume, the smaller the current flow. Thus, the DC output of circuit 22 will reflect the size of the cell interrupting or modulating the current flow. To further differentiate a particular cell type, light scattering information on each cell passing through zone Z is provided by light detector 30. Such detector is arranged to receive forward scattered light from each cell as a result of being irradiated by a laser beam B as it passes through the interrogation zone. In accordance with the present invention, the light scatter detector is designed to detect light scattered into the aforementioned five discrete angular ranges AR1–AR5 and to produce light-scatter signals LS1–LS5, respectively. In FIG. 2, a preferred detector design is shown in a top plan view. Each light-sensitive area A1–A5 is designed to receive light scattered in one of the five angular ranges AR–AR5, respectively, and each area has an output lead (not shown) on which the light scatter intensity can be measured. The respective output (DC) of the DC current-sensing circuit 22 and the five outputs signals (LS1–LS5) of light-scatter detector 30 are processed by a suitably programmed microprocessor to differentiate cells in the manner described herein.

The method of the invention will be best understood from the following working examples in which several different whole blood samples were processed by three different techniques in order to rid the sample of red blood cells and thereby provide a sample containing predominantly leukocytes. These three leukocyte samples were then processed in the same manner and according to the method of the invention to produce the five-part differential of interest. The examples serve to illustrate not only the effectiveness of the process in differentiating and enumerating cell types, but also the independence of the process on the scheme used to produce the leukocyte enriched sample that processed in accordance with the invention.

EXAMPLE 1

28 microliters of an EDTA-anticoagulated whole blood sample were dispensed into a mixing vessel. Added to and mixed with this whole blood sample for four seconds were 417 microliters of a lytic reagent comprising 0.18% formic acid, 2% of ethoxylated long chain amine represented by formula:

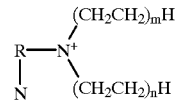

wherein R is stearyl and m+n is equal to 27. Also added to the whole blood sample and lytic reagent and mixed therewith was 1.4% of Plurafac A38 as a solubilizer and preservatives. To quench the lytic reaction, 180 microliters of a stabilizing reagent comprising 1.4% NaCl, 3.2% $Na_2SO_4$ and 0.66% $Na_2CO_3$, and having a pH of 11.0 were added. Ten seconds after the addition of the stabilizing reagent, the sample mixture was delivered to a focused flow cell on a research hematology analyzer equipped with DC volume and light scatter sensors capable of measuring light scatter intensity within the following angular ranges:

AR1=about 1.2–about 3.3 degrees
AR2=about 4.6–about 6.1 degrees
AR3=about 6.1–about 7.7 degrees
AR4=about 9.2–about 11.0 degrees
AR5=about 24–about 35 degrees.

The illumination source for light scatter measurement was a 670 nm laser diode. A sheath fluid, ISOTON® III (Coulter Corporation, Miami, Fla.) was used to hydrodynamically focus the cells within the flow cell. As the cells passed through the flow cell, DC volume measurements were made on each cell together with light scatter measurements in the above-noted angular ranges. For each cell passing through the flow cell's interrogation zone, a DC volume signal (DC) and five light-scattering signals (LS1–LS5) were produced, each light-scattering signal representing the intensity of light scattered by each cell in the angular ranges AR1–AR5.

Figure 3:
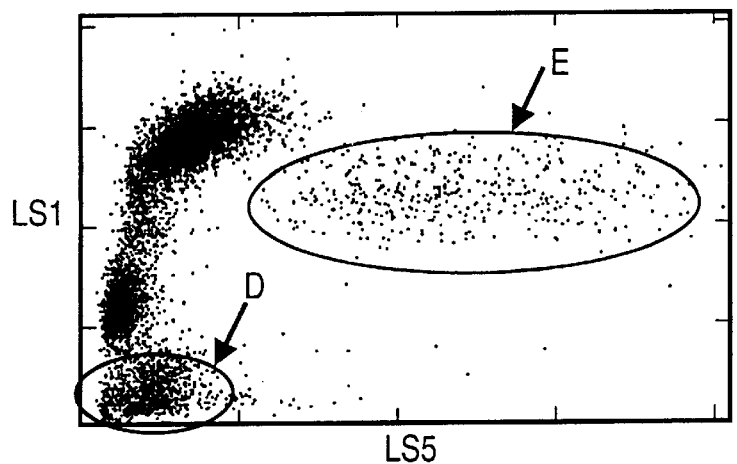
FIGS. 3–16 are scattergrams illustrating the results of the cell-differentiating method of the invention.
Figure 4:
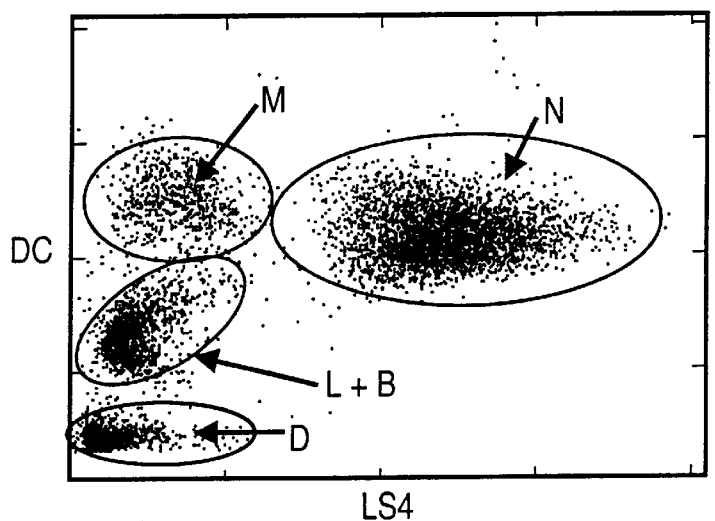
Figure 5:
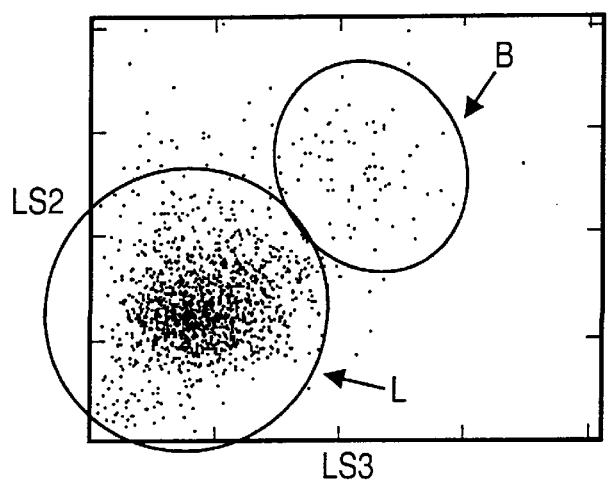

As noted above, the first step in providing a five-part analysis of leukocytes in accordance with the present invention is to differentiate and enumerate the eosinophil sub-population. FIG. 3 shows a scattergram plotting the light-scattering signals LS1 vs. LS5 representing the light scattered by each of the illuminated cells within the angular ranges AR1 and AR5. Using this scattergram, eosinophils (E) are resolved from the rest of the WBC sub-populations and red cell debris D, gated out and enumerated (counted). Referring to FIG. 4, after the eosinophils are gated out, a scattergram of DC vs. light scatter signal LS4 (representing the light scatter intensity within angular range AR4 is used to differentiate and enumerate the neutrophils (N), monocytes (M) and a third population containing both lymphocytes and basophils (L+B). For the final differentiation and enumeration of basophils (B) and lymphocytes(L), a comparison of the light-scattering signals LS2 and LS3 is used. See FIG. 5. Using this process, for example, a basophil percentage of 1.2% was measured for the blood sample processed. Using an independent method based on the aforementioned opacity (DC/RF) parameter, the basophil percentage was measured as 1.1%. The effectiveness of this approach for enumerating basophils was verified using various blood samples containing different basophil percentages.

Figure 6:
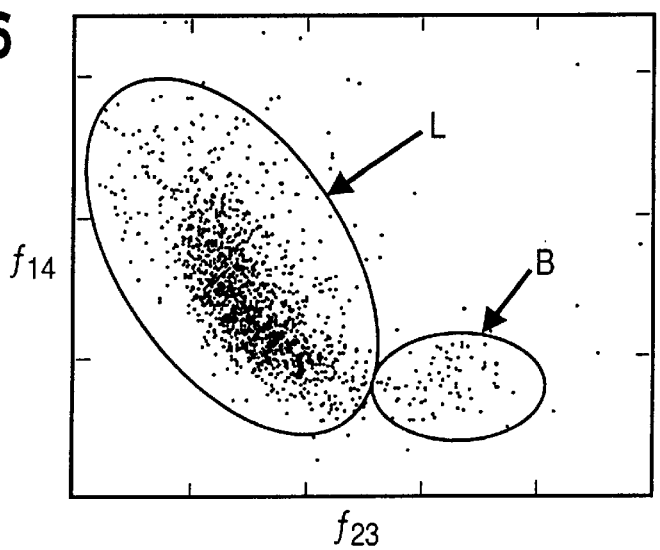

In order to separately cluster the basophils independent of the lymphocytes, the respect light scatter intensities (represented by LS2 and LS3) of each cell measured within the angular ranges AR2 and AR3 are combined by the following nonlinear transformation:

$$f_{23} = \frac{\sqrt{LS2^2 + LS3^2} \cos\left(\tan^{-1}\left(\frac{LS2}{LS3}\right) - \theta_1 \pi/180\right)}{C} - K_1$$

where $K_1$ and C are constants, and $q_1$ is an angle determined by the gains in the two light scatter channels AR2 and AR3 (typically between 30°–60°). While the basophils can be easily distinguished from the lymphocytes by plotting $f_{23}$ as a histogram, it is preferred that $f_{23}$ be plotted against the results of a second nonlinear transformation in which the light scatter intensities in angular ranges AR1 and AR4 are combined as follows:

$$f_{14} = \frac{\sqrt{LS1^2 + LS4^2} \sin\left(\tan^{-1}\left(\frac{LS4}{LS1}\right) - \theta_2 \pi/180\right)}{C} - K_2$$

where $K_2$ and C are constants, and $q_2$ is an angle determined by the gains in the two light scatter channel AR1 and AR4 (typically between 55°–70°). Comparing the parameters $f_{23}$ versus $f_{14}$ permits the basophils to be resolved as a well defined cluster separate from the lymphocytes, as seen in FIG. 6. The small cluster near the bottom right hand corner of this scatter plot, region B being the basophils. Based on the gating on this cluster in the $f_{23}$-versus-$f_{14}$ scatter plot, the lymphocyte/basophil cluster were re-plotted as a DC-opacity scattergram, which verified that the cells resolved by the $f_{23}$-versus-$f_{14}$ scattergram as basophils indeed appear in the cluster defined for the basophils by DC and opacity measurements. This confirms the correspondence between the basophil cluster resolved by the four parameter light scatter measurement (AR1–AR4) described herein, and the basophil cluster resolved by the prior art's opacity and DC measurements.

Figure 7:
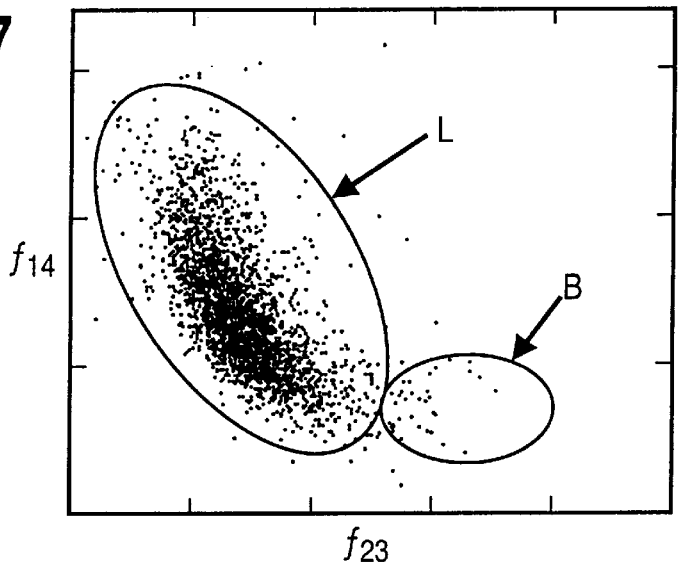
Figure 8:
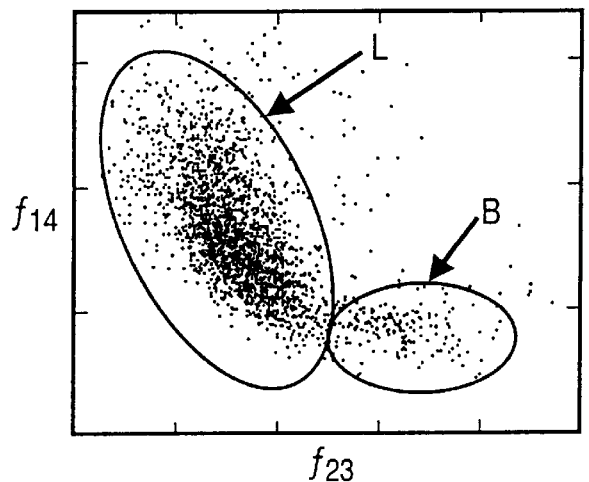

The effectiveness of this process is demonstrated graphically in FIGS. 7 and 8 using two additional and different blood samples containing different percentages of basophils. FIG. 7 shows the $f_{14}$ vs. $f_{23}$ scattergram of a sample for which a basophil percentage of 0.89% was measured by the present light scatter-based method. Independent measurement by opacity measured 0.69% basophils for this sample. FIG. 8 shows a $f_{14}$ VS. $f_{23}$ scattergram of a sample for which an independent measurement by opacity measured a basophil percentage of 1.88%. For this same sample, the present light scatter-based method produced a result for a basophil percentage of 1.81%.

EXAMPLE 2

1 ml of whole blood was gently pipetted on top of 5 ml Histopaque 1077 in a test tube and allowed to rest for approximately 45 min. Due to density gradients, the red blood cells transport downwards through the Histopaque-1077 settling at the bottom of the tube, leaving the white blood cells in the plasma at the top of the Histopaque layer. The white cells were pipetted out gently from this top layer, diluted in a isotonic solution (15 microliter in 2 ml ISOTON) and the sample suspension was run immediately in a hematology analyzer equipped with DC impedance and light scatter sensors capable of measuring light scatter intensity at the above angles (i.e., AR1–AR5). The illumination source for light scatter measurement was a 670 nm laser diode.

Figure 9:
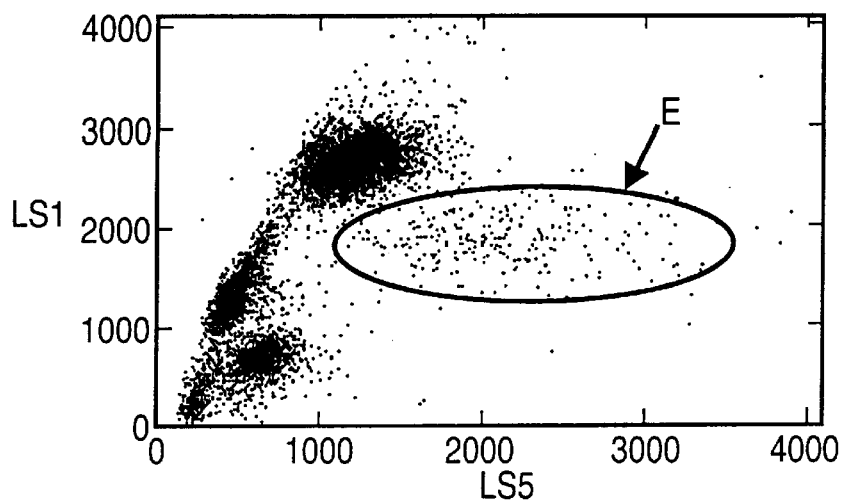
Figure 10:
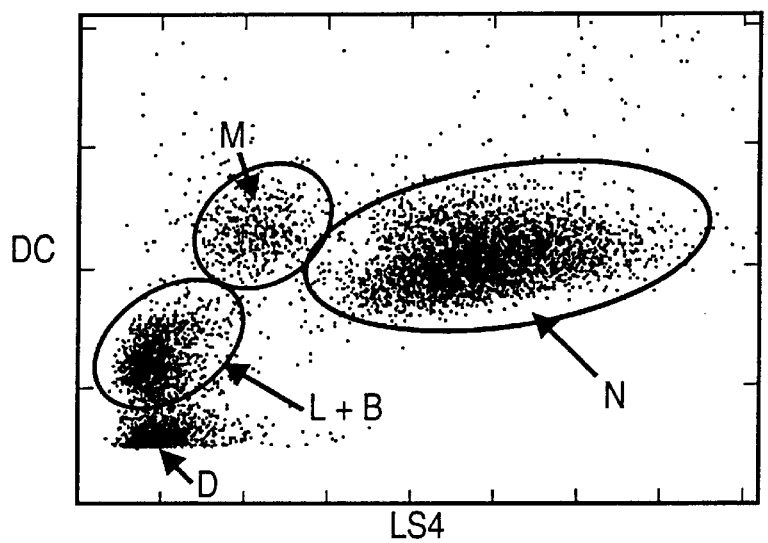
Figure 11:
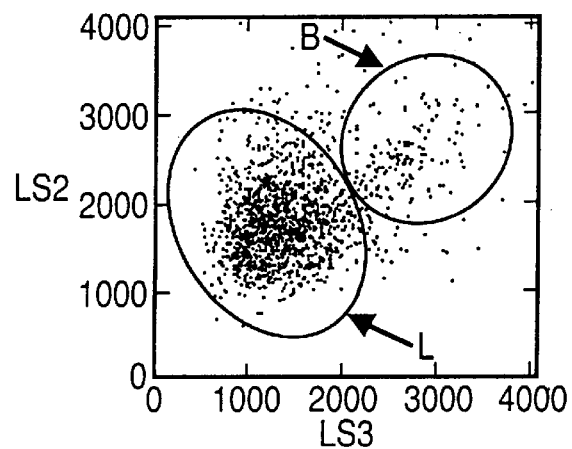
Figure 12:
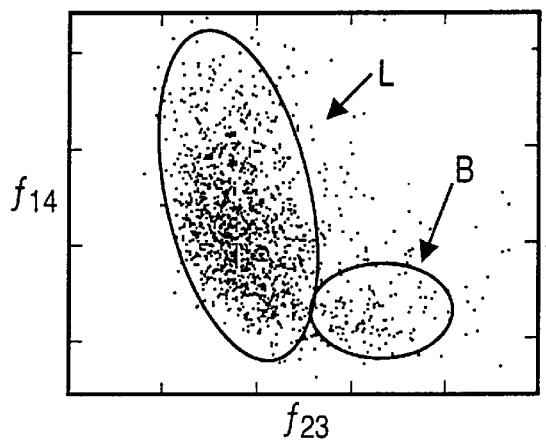

FIG. 9 shows a scattergram of LS1 vs. LS5 for the white blood cell sample extracted from whole blood by this method. Using the above-described method of the invention, eosinophils (E) were first resolved from the rest of the WBC sub-populations. After the eosinophils are gated out from the rest, a scattergram of DC vs. LS4 (FIG. 10) is used to enumerate the neutrophils, monocytes and the third population containing both lymphocytes and basophils. For the final enumeration of basophils and lymphocytes separately, a comparison of the parameters LS2 vs. LS3 was used (FIG. 11). The enhanced clustering approach for resolving the basophil sub-population from the lymphocytes by comparing the transformed parameter $f_{14}$ vs. $f_{23}$ (as shown in FIG. 12) was used.

EXAMPLE 3

To 28 microliters of an EDTA-anticoagulated whole blood sample was added 512 microliters of a lytic reagent comprising 1.2 ml/L formic acid and 0.3–1.5 ml/L of saponin, and mixed for about 5–8 sec. This lytic reagent is available from Coulter Corporation, Miami, Fla. under the trademark Erythrolyse. Then 208 microliters of a leukocyte preservative stabilizing reagent containing 9.0 g/L $Na_2CO_3$, 14.5 g/L NaCl, and 33.3 g/L $Na_2SO_4$, and having a pH of 11.0 was added and mixed to retard lytic reaction.

About eleven seconds after the addition of the stabilizing reagent the sample mixture was delivered to a focused flow cell with a sheath fluid, ISOTON III diluent (Coulter Corporation, Miami, Fla.) on a research hematology analyzer of the type used in Examples 1 and 2 above.

Figure 13:
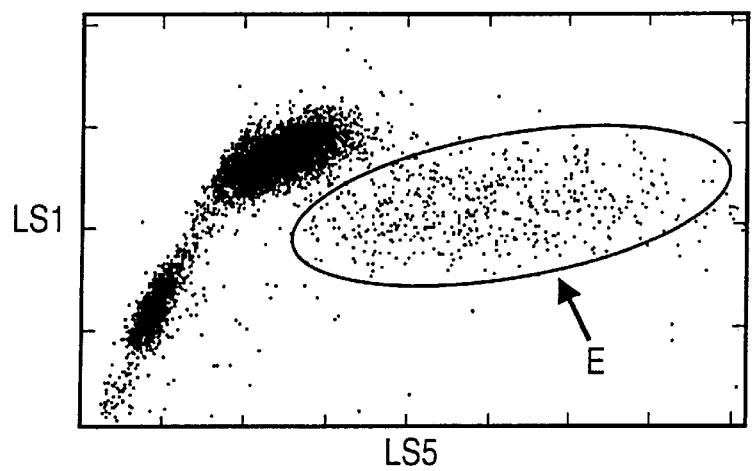
Figure 14:
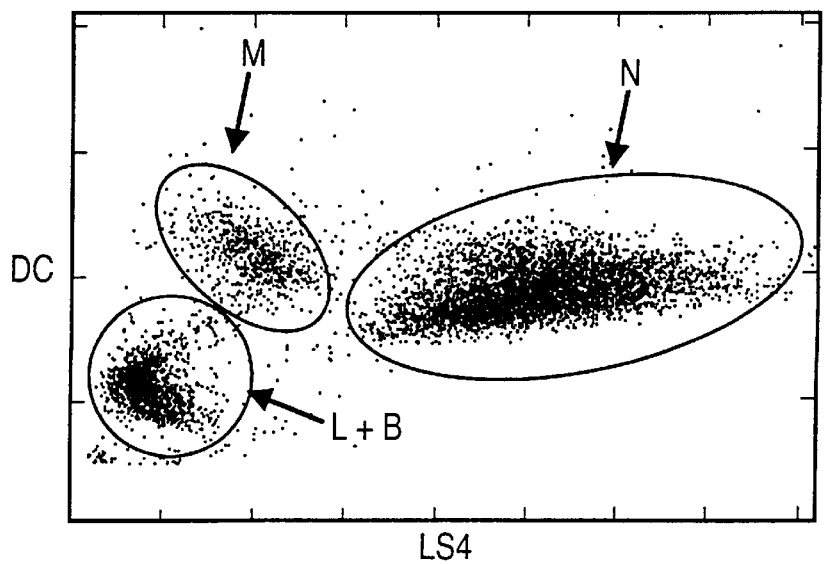
Figure 15:
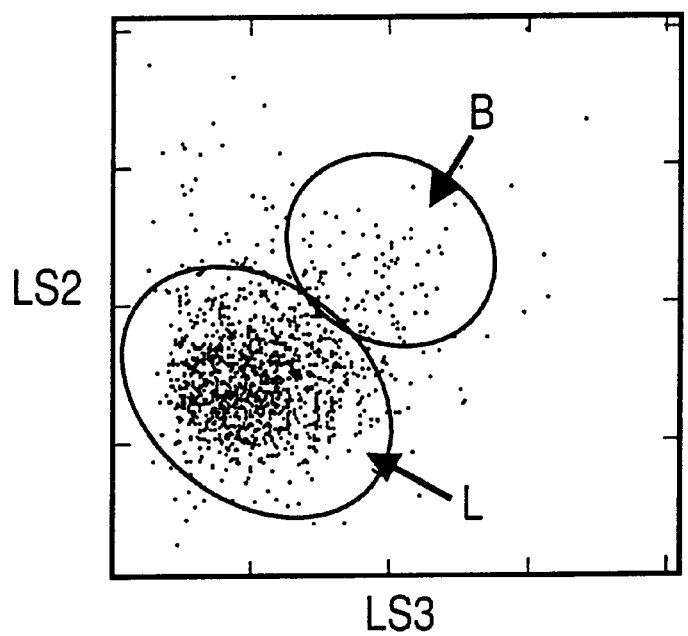
Figure 16:
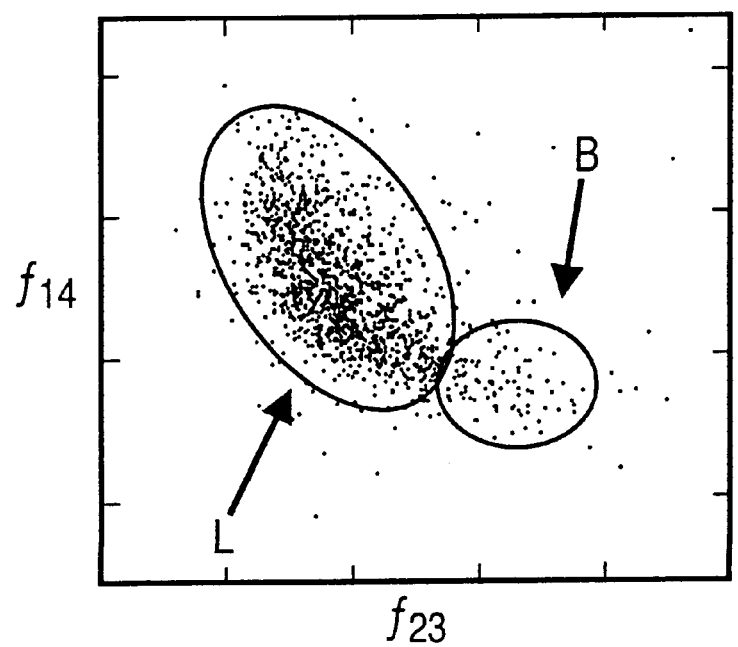

FIG. 13 shows a scattergram of LS1 vs. LS5 for the blood sample passing through the flow cell following treatment with the Erythrolyse reagent. Using this view, similarly to the procedure described for Example 1 and Example 2 above, eosinophils are first resolved from the rest of the WBC sub-populations. After the eosinophils are gated out from the rest of the leukocytes, a scattergram of DC vs. LS4 (FIG. 14) is used to enumerate the neutrophils, monocytes, and a third population containing both lymphocytes and basophils. For the final enumeration of basophils and lymphocytes separately, a comparison of the parameters LS2 vs. LS3 was used (FIG. 15). The enhanced clustering approach for resolving the basophil sub-population from the lymphocytes by comparing the transformed parameter $f_{14}$ vs. $f_{23}$ (as shown in FIG. 16) was used.

The invention has been described with reference to preferred embodiments. Certain obvious variations will be self-evident without departing from the spirit of the invention, and such variations are intended to fall within the scope of the following claims.

What is claimed is:

1. A method for differentiating and enumerating five different sub-populations of leukocytes in a blood sample containing said leukocytes, said method comprising the steps of (a) producing first electrical signals representative of the relative volume of individual leukocytes in the blood sample, (b) producing a plurality of second electrical signals representative of light-scattering properties of said individual leukocytes within five different angular ranges, each of such angular ranges being lower than 40 degrees measured with respect to a direction of propagation of a cell-illuminating light beam, and (c) differentiating and enumerating said sub-populations of leukocytes based on said first and second signals.

2. The method as defined by claim 1 wherein said five different angular ranges (AR1–AR5) are as follows:

AR1=between about 1 and about 3 degrees;
AR2=between about 4 and about 6 degrees;

AR3=between about 6 and about 8 degrees;
AR4=between about 9 and about 12 degrees; and
AR5=between about 20 and about 40 degrees.

3. The method as defined by claim 1 wherein an eosinophil sub-population of leukocytes is differentiated from other leukocytes by the steps of:
   (a) illuminating the leukocytes in said sample, one at a time, with a unidirectional beam of light;
   (b) detecting the intensity of light scattered by said leukocytes within the following two angular ranges: (i) between about 1 degree and about 3 degrees, and (ii) between about 20 degrees and about 40 degrees; and
   (c) differentiating eosinophils from other leukocytes based on the intensity of scattered light within said two angular ranges.

4. A method for differentiating basophils from lymphocytes in a whole blood sample containing both basophils and lymphocytes, said method comprising the steps of:
   (a) illuminating the basophils and lymphocytes in said sample, one at a time, with a unidirectional beam of light;
   (b) detecting the intensity of light scattered by each illuminated basophil and lymphocyte within the following angular ranges: (i) from about 4 to about 6 degrees; and (ii) from about 6 to about 8 degrees; and
   (c) differentiating basophils from lymphocytes on the basis of the light scatter intensity detected within said angular ranges.

5. The method as defined by claim 4 wherein said basophils are further differentiated from lymphocytes by the additional steps of:
   (d) detecting the intensity of light scattered by each illuminated cell within the following additional angular ranges: (i) from about 1 to about 3 degrees; and (ii) from about 9 to about 11 degrees; and
   (e) differentiating basophils from lymphocytes on the basis of the intensities detected in step (d).

6. A method for differentiating and enumerating the basophil sub-population of leukocytes in a whole blood sample containing basophils and other leukocytes, said method comprising the steps of:
   (a) individually irradiating each of the leukocytes in said whole blood sample with a unidirectional beam of radiation to cause each of the irradiated leukocytes to scatter a portion of the radiation incident thereon at angles determined by the physical characteristics of the irradiated leukocyte;
   (b) detecting the respective intensities of the radiation scattered by each of said leukocytes within a plurality of discrete angular ranges, each of said ranges being within about 4 degrees and about 8 degrees measured with respect to the direction of said unidirectional beam; and
   (c) differentiating and enumerating the basophil sub-population solely from said detected intensities.

7. The method as defined by claim 6 wherein said plurality of angular ranges comprise two angular ranges, one of said angular ranges being between about 4 degrees and about 6 degrees, and the other angular range being between about 6 degrees and about 8 degrees.

8. The method as defined by claim 6 wherein said differentiating step comprises producing a scattergram plotting the respective intensities of scattered radiation in one of said plurality of angular ranges versus the respective intensities of scattered radiation in another of said plurality of angular ranges.

9. A method for differentiating lymphocytes, monocytes, eosinophils, neutrophils and basophils in a whole blood sample, said method comprising the steps of
   (a) subjecting a whole blood sample to a lysing reagent to provide a lysed sample containing predominantly white blood cells;
   (b) providing an optical flow cell having a cell interrogation zone in which blood cells comprising a blood sample to be analyzed can be interrogated with optical and electrical energy;
   (c) causing white blood cells in the lysed sample to pass through the interrogation zone seriatim;
   (d) establishing a DC current flow through the interrogation zone while blood cells are passing therethrough, each of the blood cells being effective to modulate the DC current in the interrogation zone as a function of the cell's volume;
   (e) detecting the respective modulations in the DC current flow caused by the passage of individual cells passing through the interrogation zone and producing electrical signals proportional to a characteristic of such modulations;
   (f) irradiating individual blood cells passing through the interrogation zone with a beam of radiation propagating along an axis, each irradiated cell acting to scatter radiation incident thereon;
   (g) detecting the intensity of radiation scattered from an irradiated blood cell in the interrogation zone within the following plurality of different angular ranges AR1–AR5 measured with respect to, and in a plane normal to, the beam axis, and providing discrete electrical signals proportional to the intensity of scattered radiation in each different angular range:
   AR1=between about 1 and 3 degrees;
   AR2=between about 4 and 6 degrees;
   AR3=between about 6 and 8 degrees;
   AR4=between about 9 and 12 degrees;
   AR5=between about 20 and 40 degrees; and
   (h) differentiating lymphocytes, monocytes, neutrophils, eosinophils and basophils, based on the respective amplitudes of the respective electrical signals produced by steps (e) and (g).

10. Apparatus for differentiating lymphocytes, monocytes, eosinophils, neutrophils and basophils in a blood sample, said apparatus comprising:
   (a) a flow cell defining a passageway through which individual blood cells in a blood sample can be made to flow seriatim;
   (b) means for causing said blood cells to flow through said passageway seriatim;
   (c) first circuit means for establishing a DC current flow through said passageway while blood cells are flowing therethrough, each of said blood cells being effective to modulate the DC current in said passageway as a function of the cell's volume;
   (d) second circuit means for detecting modulations in said DC current and for producing a first electrical signal proportional to the amplitude of said modulations;
   (e) optical means for irradiating individual blood cells flowing through said passageway with a beam of radiation propagating along an axis;

(f) radiation scatter-detecting means for detecting radiation scattered from an irradiated blood cell in said passageway, said radiation scatter detecting means comprising an array of photo-detectors adapted to detect scattered radiation within the following plurality of different angular ranges measured with respect to, and in a plane normal to, said axis:
AR1=between about 1 and 3 degrees
AR2=between about 4 and 6 degrees
AR3=between about 6 and 8 degrees
AR4=between about 9 and 12 degrees
AR5=between about 20 and 40 degrees;
each of said photo-detectors operating to provide a signal proportional to the intensity of scattered radiation detected thereby; and (g) analyzing means, operatively coupled to said second circuit means and to said photo-detectors for differentiating said lymphocytes, monocytes, neutrophils, eosinophils and basophils in said blood sample based on the respective amplitudes of the respective signals produced by said second circuit and by said photo-detectors.

* * * * *